(12) United States Patent
Ongini et al.

(10) Patent No.: US 7,858,665 B2
(45) Date of Patent: Dec. 28, 2010

(54) DRUGS FOR CHRONIC PAIN

(75) Inventors: Ennio Ongini, Milan (IT); Nicoletta Almirante, Milan (IT); Piero Del Soldato, Milan (IT)

(73) Assignee: Nicox S.A., Sophia Antipolis Cedex (FR)

( * ) Notice: Subject to any disclaimer, the term of this patent is extended or adjusted under 35 U.S.C. 154(b) by 0 days.

(21) Appl. No.: 12/476,717

(22) Filed: Jun. 2, 2009

(65) Prior Publication Data
US 2009/0239832 A1 Sep. 24, 2009

Related U.S. Application Data

(63) Continuation of application No. 10/537,439, filed as application No. PCT/EP03/050932 on Dec. 3, 2003, now Pat. No. 7,642,289.

(30) Foreign Application Priority Data

Dec. 17, 2002 (IT) .......................... MI2002A2658

(51) Int. Cl.
*A61K 31/16* (2006.01)
*A61K 31/166* (2006.01)
*C07C 229/04* (2006.01)
*C07C 229/28* (2006.01)

(52) U.S. Cl. ..................... 514/615; 514/662; 562/450

(58) Field of Classification Search ................. 514/615, 514/662; 562/480, 450
See application file for complete search history.

(56) References Cited

FOREIGN PATENT DOCUMENTS

| WO | WO 95/09831 A1 | 4/1995 |
|---|---|---|
| WO | WO 95/30641 A1 | 11/1995 |
| WO | WO 97/16405 | 5/1997 |
| WO | WO 00/54773 A1 | 9/2000 |
| WO | WO 00/76958 A2 | 12/2000 |
| WO | WO 01/12584 A2 | 2/2001 |
| WO | WO 01/90052 A1 | 11/2001 |
| WO | WO 02/11707 A2 | 2/2002 |
| WO | WO 03/000642 A2 | 1/2003 |

OTHER PUBLICATIONS

Gary J. Bennett, et al.; A Peripheral Mononeuropathy in Rat That Produces Disorders of Pain Sensation Like Those Seen in Man; Neurobiology and Anesthesiology Branch, National Institute of Dental Research, National Institutes of Health, Bethesda, MD, Pain, 33 (1988), pp. 87-107, Elsevier, USA.

M.W. Radomski, et al; The Anti-Aggregating Properties of Vascular Endothelium: Interactions Between Prostacyclin and Nitric Oxide, The Wellcome Research Laboratories, Langley Court, Beckenham, Kent BR3 3BS, The Macmillan Press Ltd 1987, pp. 640-646.

James E. F. Reynolds, et al.; Martindale the Extra Pharmacopoeia, Thirtieth Edition, The Pharmaceutical Press, London, 1993 p. 374.

*Primary Examiner*—Rebecca L Anderson
*Assistant Examiner*—Shawquia Young
(74) *Attorney, Agent, or Firm*—Arent Fox LLP

(57) ABSTRACT

The present invention relates to nitrooxyderivatives or salts thereof having the following general formula (I):

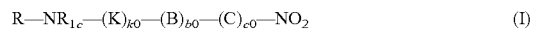

wherein
c0, b0 and k0 are 0 or 1;
R is the radical of an analgesic drug for chronic pain, for instance neurophatic pain;
$R_{1c}$ is H or alkyl with from 1 to 5 carbon atoms;
B is such that its precursor is selected from amino acids, hydroxy acids, polyalcohol, compounds;
C is a bivalent radical containing an aliphatic, heterocyclic or aromatic radical.

7 Claims, No Drawings

DRUGS FOR CHRONIC PAIN

CROSS-REFERENCE TO RELATED APPLICATION

This application is a continuation of U.S. patent application Ser. No. 10/537,439 filed Jun. 16, 2005, which is a National Stage entry of International Application No. PCT/EP03/050932, filed Dec. 3, 2003, which claims priority to Italian Patent Application No. MI2002A002658 filed Dec. 17, 2002, the entire specification and claims which are incorporated herewith by reference.

The present invention relates to compounds having an improved effectiveness in reducing the chronic pain, specifically the neurophatic pain. In order to describe chronic pain, for simplicity always reference to neuropathic pain will be made.

It is known that neurophatic pain is a form of chronic pain arising from a damage or disease of the central or peripheral nervous system. Neurophatic pain comprises a series of painful symptomatologies such as diabetic neurophatic pain, painful post-infarct syndrome, pain caused by chemotherapeutic treatment or pain arising from infections by viral agents, for example herpes, for instance Herpes zoster, etc.

Neurophatic pain generally affects patients for many years, and is a social problem in that symptoms chronicity induces in subjects serious psychological stress.

In last twenty years, research on neurophatic pain pathogenesis has achieved notable advances. Studies carried out on human and animal experimental models of neurophatic pain have shown that central nervous system reacts to algogen stimuli with a series of biochemical and physiopathologic responses. This ability of the central nervous system to functionally and morphologically adapt to algogen stimuli is known as neuroplasticity and plays an essential role in inducing onset or in maintaining the painful symptomatology.

The usual analgesic drugs actually employed for treating chronic pain are partially or absolutely not effective.

Carbamazepine, that has been widely used in clinical studies, has shown to be active in treating trigeminal neuralgia, diabetic neurophatic pain, and post-herpetic neuralgia. The administration of this drug has the drawback to present side effects such as somnolence, dizziness, ataxy, nausea and vomiting, thus limiting its use.

In last years, further drugs for the treatment of neuropathic pain have been tested. Among these in particular gabapentin can be mentioned, that is very active as analgesic drug for treating neuropathic pain, mainly against diabetic neurophatic pain and post-herpetic pain. However, also in this case serious adverse effects have been observed, for example somnolence, weariness, obesity, etc. (Martindale XXXth Ed, page 374).

It was thus object of the present invention to provide drugs having an improved pharmacotherapeutic profile and/or lower side effects in the treatment of chronic pain, in particular neurophatic pain.

It has been now surprisingly and unexpectedly found from the Applicant that this problem can be solved with the class of drugs described below.

The present invention relates to nitrooxyderivatives or salts thereof having the following general formula (I):

$$R-NR_{1c}-(K)_{k0}-(B)_{b0}-(C)_{c0}-NO_2 \quad (I)$$

wherein c0 is 0 or 1, preferably 1;

b0 is 0 or 1, with the proviso that c0 and b0 can not be simultaneously 0;

k0 is 0 or 1;

R is the radical of an analgesic drug for chronic pain, for instance neurophatic pain;

$R_{1c}$ being H or straight or branched alkyl with from 1 to 5 carbon atoms;

K is (CO) or the bivalent radical (1C) having the following formula:

(1-C)

wherein the carbonyl group is bound to $T_1$; $R_t$ and $R'_t$, same or different, are H, $C_1$-$C_{10}$-alkyl, phenyl or benzyl, —COOR$_y$, in which $R_y$=H, $C_1$-$C_{10}$-alkyl, phenyl, benzyl;

$B = -T_B-X_2-T_{BI}-$ wherein $T_B$=(CO) or X, in which X=O, S, NH;

with the proviso that:

when b0=1 and k0=0, then $T_B$=(CO);

when b0=1 and k0=1, being K=(CO), then $T_B$=X as defined above;

$T_{BI}$=(CO) or (X), wherein X is as defined above;

when c0=0, then $T_{BI}$=—O—;

$X_2$ is such a bivalent bridging group such as the corresponding precursor of B, having the formula Z-$T_B$-$X_2$-$T_{BI}$-Z' in which Z, Z' are independently H or OH, is selected from the following compounds:

Aminoacids: L-carnosine (CI), penicillamine (CV), N-acetylpenicillamine (CVI), cysteine (CVII), N-acetylcysteine (CVIII):

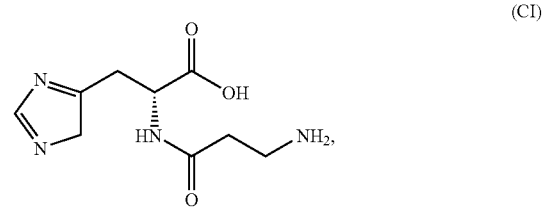

(CI)

(CV)

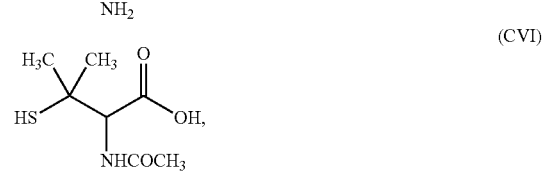

(CVI)

(CVII)

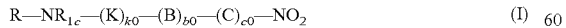

-continued

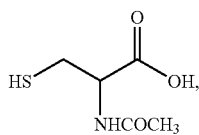
(CVIII)

Hydroxyacids: gallic acid (DI), ferulic acid (DII), gentisic acid (DIII), caffeic acid (DV), hydro caffeic acid (DVI), p-coumaric acid (DVII), vanillic acid (DVIII), syringic acid (DXI):

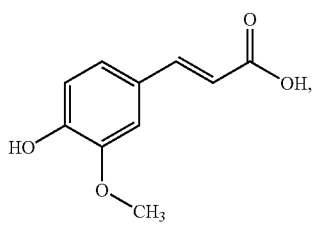
(DII)

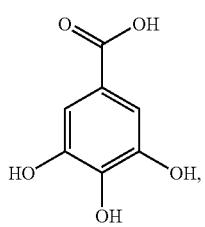
(DI)

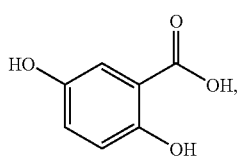
(DIII)

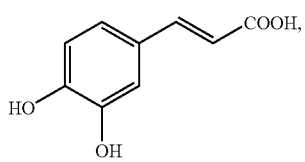
(DV)

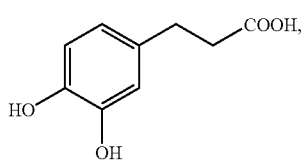
(DVI)

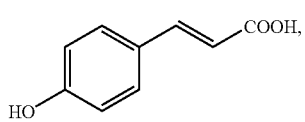
(DVII)

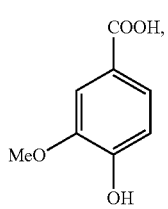
(DVIII)

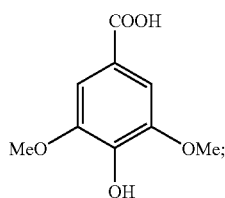
(DXI)

aromatic polyalcohols: hydroquinone (EVIII), methoxy-hydroquinone (EXI), hydroxyhydroquinone (EXII), conyferyl alcohol (EXXXII), 4-hydroxyphenetyl alcohol (EXXXIII), p-coumaric alcohol (EXXXIV):

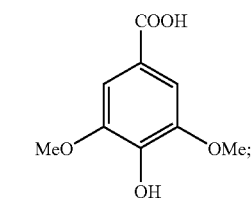
(EVIII)

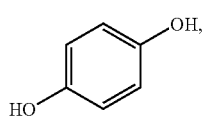
(EXI)

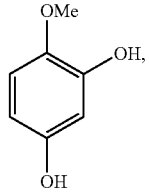
(EXII)

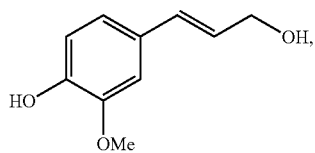
(EXXXII)

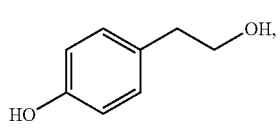
(EXXXIII)

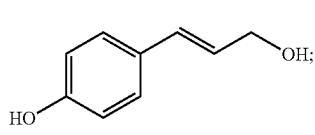
(EXXXIV)

C=bivalent radical having the formula -$T_c$-Y— wherein $T_c$=(CO) or X being as defined above;

with the proviso that when b0=0 and k0=1:
    $T_c$=(CO) when K=(1C),
    $T_c$=X as defined above when K=(CO);

Y has one of the following meanings:

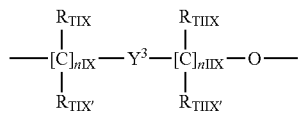
(III)

wherein:

nIX is an integer of from 0 to 5, preferably from 1;

nIIX is an integer of from 1 to 5, preferably from 1;

$R_{TIX}$, $R_{TIX'}$, $R_{TIIX}$, $R_{TIIX'}$, the same or different, are H or straight or branched $C_1$-$C_4$-allkyl; preferably $R_{TIX}$, $R_{TIX'}$, $R_{TIIX}$, $R_{TIIX'}$ are H;

$Y^3$ is a saturated, unsaturated or aromatic heterocyclic ring with 5 or 6 atoms, containing one to three heteroatoms, preferably one or two, said heteroatoms being the same or different and selected from nitrogen, oxygen or sulphur;

or Y may be:

an alkylenoxy group —R'O— in which R' is straight or branched $C_1$-$C_{20}$, preferably with from 2 to 6 carbon atoms, or a cycloalkylene with from 5 to 7 carbon atoms, and wherein in cycloalkylene ring one or more carbon atoms can be replaced by heteroatoms and the ring may present side chains of R' type, R' being as defined above; or one of the following groups:

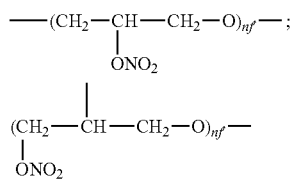

wherein nf' is an integer from 1 to 6, preferably from 1 to 4;

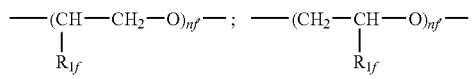

wherein $R_{1f}$=H, $CH_3$ and nf' is an integer from 1 to 6; preferably from 1 to 4;

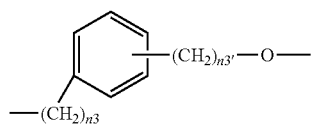

wherein n3 is an integer from 0 to 5 and n3' is an integer from 1 to 3; or

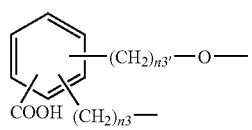

in which n3 and n3' have the meaning mentioned above.

Radical R in formula (I) is preferably a radical of chronic analgesic drugs, in particular drugs for neurophatic pain, and it can be selected from the usual products available on the market for said use. The tricyclic antidepressant and antiepileptic drugs can be mentioned.

R is the radical of an analgesic drug having formula (II):

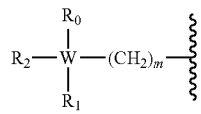

wherein:

W is a carbon or nitrogen atom;

m is an integer of from 0 to 2;

$R_0$=H, —$(CH_2)_n$—$COOR_y$, $R_y$ being as defined above;

n is an integer of from 0 to 2;

$R_1$=H; when W=N, $R_1$ is the electronic doublet on nitrogen atom (free valence);

$R_2$ is selected from the following groups:
 phenyl, optionally substituted with a halogen atom or with a group selected from —$OCH_3$, —$CF_3$, nitro;
 mono or dihydroxy-substituted benzyl, preferably 3,4-dihydroxybenzyl;
 amidino group: $H_2N(C=NH)$—;
 a radical of formula (IIA), wherein optionally an ethylenic unsaturation may be present between the carbon atoms in position 1 and 2, or 3 and 4 or 4 and 5:

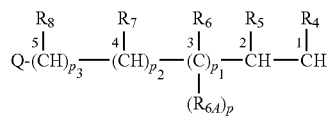
(IIA)

wherein:

p, $p_1$, $p_2$ are integers, same or different, and are 0 or 1;

$p_3$ in an integer of from 0 to 10;

$R_4$ is hydrogen, straight or branched $C_1$-$C_6$-alkyl, free valence;

$R_5$ may have the following meanings:
 hydrogen,
 straight or branched $C_1$-$C_6$-alkyl,
 $C_3$-$C_6$-cycloalkyl,
 $OR_A$, $R_A$ having the following meanings:
  straight or branched $C_1$-$C_6$-alkyl, optionally substituted with one or more halogen atoms, preferably F,
  phenyl optionally substituted with a halogen atom or with one of the following groups: —$OCH_3$, —$CF_3$, nitro;

$R_6$, $R_{6A}$, $R_7$, $R_8$, the same or different, are H, methyl or free valence, with the proviso that when an ethylenic unsaturation is present between $C_1$ and $C_2$ in radical of formula (IIA), $R_4$ and $R_5$ are free valences able to form the double bond between $C_1$ and $C_2$; if the unsaturation is between $C_3$ and $C_4$, $R_6$ and $R_7$ are free valence able to form the double bond between $C_3$ and $C_4$; is the unsaturation is between $C_4$ and $C_5$, $R_7$ and $R_8$ are free valence able to form the double bond between $C_4$ and $C_5$;

Q is H, OH, $OR_B$, $R_B$ being benzyl, straight or branched $C_1$-$C_6$-alkyl, optionally substituted with one or more halogen atoms, preferably F, phenyl optionally substituted with a halogen atom or with one of the following groups: —OCH₃, —CF₃, nitro;

or Q may have one of the following meanings:
straight or branched $C_1$-$C_6$-alkyl,
$C_3$-$C_6$-cycloalkyl,
guanidino ($H_2NC(=NH)NH—$),
thioguanidino ($H_2NC(=S)NH—$);

in formula (II) $R_2$ with $R_1$ and with W=C form together a $C_4$-$C_{10}$ saturated or unsaturated ring, preferably a $C_6$ saturated one.

When in formula (II) W=C, m=1 and $R_0$=—$(CH_2)_n$—$COOR_y$, wherein n=1 and $R_y$=H; $R_2$ and $R_1$ with W as defined above form the cyclohexane ring; the drug precursor of R having the formula R—NH₂ is known as gabapentin;

when in formula (II) W=C, m=0 and $R_0$ if defined as for gabapentin with n=0; $R_1$=H; $R_2$ is the radical of formula (IIA) in which p=$p_1$=1, $p_2$=$p_3$=0, $R_4$=$R_5$=$R_6$=$R_{6A}$=H, Q=H; the drug precursor of R having the formula R—NH₂ is known as norvaline;

when in formula (II) W=C, m=0 and $R_0$ if defined as for gabapentin with n=0; $R_1$=H; $R_2$ is the radical of formula (IIA) in which p=$p_1$=1, $p_2$=$p_3$=0, $R_4$=$R_5$=$R_6$=$R_{6A}$=H, Q is the guanidino group; the drug precursor of R having the formula R—NH₂ is known as arginine;

when in formula (II) W=C, m=0 and $R_0$ if defined as for gabapentin with n=0; $R_1$=H; $R_2$ is the radical of formula (IIA) in which p=$p_1$=1, $p_2$=$p_3$=0, $R_4$=$R_5$=$R_6$=$R_{6A}$=H, Q is the thioguanidino group; the drug precursor of R having the formula R—NH₂ is known as thiocitrulline;

when in formula (II) W=C, m=1 and $R_0$ if defined as for gabapentin with n=1; $R_1$=H; $R_2$ is the radical of formula (IIA) in which p=$p_1$=$p_2$=$p_3$=0, $R_4$=H, $R_5$=Q=$CH_3$; the drug precursor of R having the formula R—NH₂ is known as pregabalin;

when in formula (II) W=C and has (S) configuration, m=1 and $R_0$ if defined as for gabapentin with n=1; $R_1$=H; $R_2$ is the radical of formula (IIA) in which p=$p_1$=$p_2$=$p_3$=0, $R_4$=H, $R_5$=Q=$CH_3$; the drug precursor of R having the formula R—NH₂ is known as (S)3-isobutilGABA;

when in formula (II) W=C and has (S), m=0; $R_0$=$R_1$=H; $R_2$ is the radical of formula (IIA) in which p=$p_1$=1, $p_2$=$p_3$=0, $R_4$=$R_5$=$R_6$=$R_{6A}$=H, Q is the guanidino group; the drug precursor of R having the formula R—NH₂ is known as agmatine;

when in formula (II) W=C, m=0; $R_0$ if defined as for gabapentin with n=2; $R_1$=H; $R_2$ is the radical of formula (IIA) in which p=$p_1$=$p_2$=$p_3$=0, $R_4$ and $R_5$ are free valences and between $C_1$ and $C_2$ there is an ethylenic unsaturation, Q=H; the drug precursor of R having the formula R—NH₂ is known as vigabatrin;

when in formula (II) W=C, m=0; $R_0$ if defined as for gabapentin with n=0; $R_1$=H; $R_2$ is the 3,4-dihydroxybenzyl radical; the drug precursor of R having the formula R—NH₂ is known as 2-amino-3-(3,4-dihydroxyphenylpropanoic acid (dopa).

Further compounds employed for chronic pain and that can be used as precursors of R in formula (I) are lamotrigine, topiramate, zonisamide, carbamazepine, felbamate, amineptine, amoxapine, demexiptiline, desipramine, nortriptyline, tianeptine.

Generally, the drug precursors of R are synthesized according to the procedures described in "The Merck Index, 12ᵗʰ Ed." (1996). When the drug precursors of R present in the molecule present the radical of formula (IIA), they can be obtained as described in WO 00/79658.

The precursor compounds of B falling within the groups mentioned above can be synthesized according to methods well known in literature and mentioned for example in "The Merck Index, 12ᵗʰ Ed.", here incorporated in full for reference.

In formula (III), $Y^3$ is selected from the following bivalent radicals:

 (Y1)

 (Y2)

 (Y3)

 (Y4)

 (Y5)

 (Y6)

 (Y19)

 (Y7)

 (Y8)

 (Y9)

 (Y10)

 (Y11)

 (Y18)

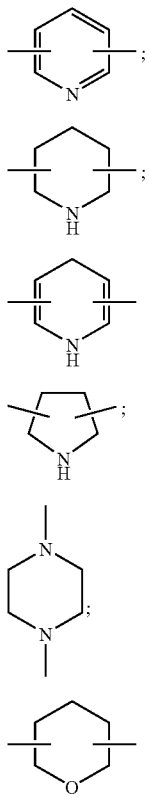

(Y12)

(Y13)

(Y14)

(Y15)

(Y16)

(Y17)

Preferred among the $Y^3$ meanings are the following: (Y12), having both the free valences in ortho position as to the nitrogen atom; (Y16) with both the valences attached to the heteroatoms, Y1 (pyrazole) 3,5-disubstituted.

The Y precursors as defined by formula (III), in which the oxygen free valence is saturated with H and the endstanding carbon atom free valence is saturated with a carboxylic or hydroxylic group, are products available on the market or they can be obtained according to well known procedures.

In formula (I), the B precursors preferred for synthesizing the nitrooxyderivatives to be employed in the present invention are the following: ferulic acid and N-acetylcysteine, the preferred drug precursors being gabapentin, norvaline, arginine, pregabalin, (S)-3-isobutylGABA, agmatine and vigabatrin.

The preferred compounds of formula (I) of the present invention are the following:

1-[4-(nitrooxymethyl)benzoylaminomethyl]-cyclohexaneacetic acid (XVA),

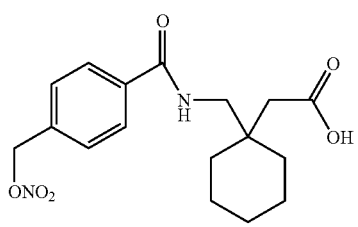

(XVA)

1-[3-(nitrooxymethyl)benzoylaminomethyl]-cyclohexaneacetic acid (XVIA),

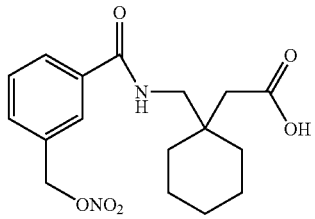

(XVIA)

1-[2-(nitrooxymethyl)benzoylaminomethyl]-cyclohexaneacetic acid (XVIIA),

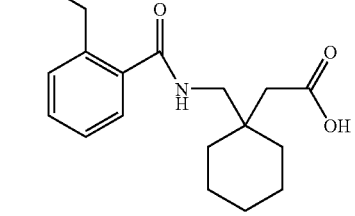

(XVIIA)

1-(4-nitrooxybutanoylaminomethyl)-cyclohexaneacetic acid (XVIIIA),

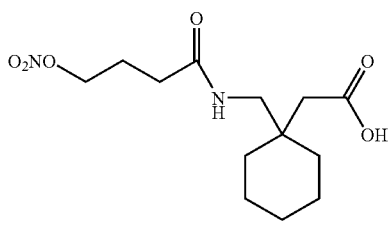

(XVIIIA)

1-(nitrooxymethoxycarbonylaminomethyl)-cyclohexaneacetic acid (XIXA),

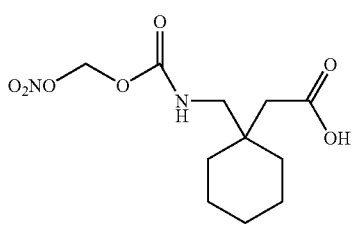

(XIXA)

1-{[4-(nitrooxymethyl)benzoyloxy]methoxycarbonylaminomethyl}-cyclohexaneacetic acid (XXA),

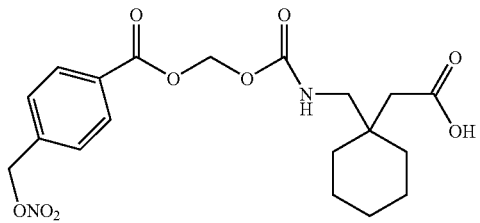

(XXA)

1-{[3-(nitrooxymethyl)benzoyloxy]methoxycarbonylaminomethyl}-cyclohexaneacetic acid (XXIA),

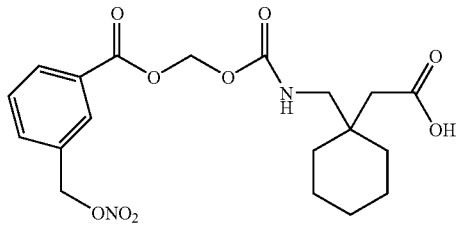

1-{[2-(nitrooxymethyl)benzoyloxy]methoxycarbonylaminomethyl}-cyclohexaneacetic acid (XXIIA),

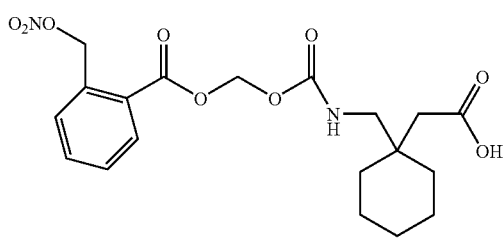

1-[3-(nitrooxymethyl)phenoxycarbonylaminomethyl]-cyclohexaneacetic acid (XXIIIA),

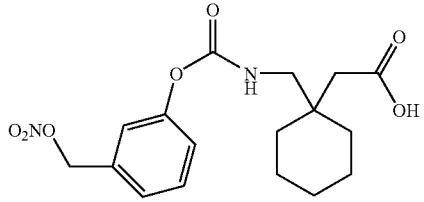

{2-methoxy-4-[(1E)-3-[4-(nitrooxybutoxy)-3-oxa-1-propenylphenoxy]-carbonylamino-methyl}-cyclohexaneacetic acid (XXIVA),

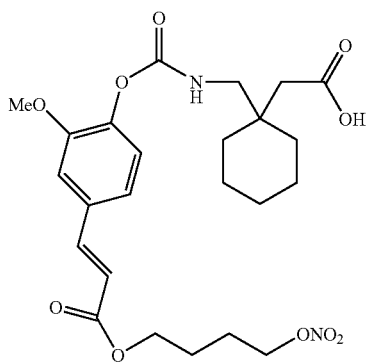

3-(S)-[4-(nitrooxymethyl)benzoylaminomethyl]-5-methyl-hexanoic acid (XXVA),

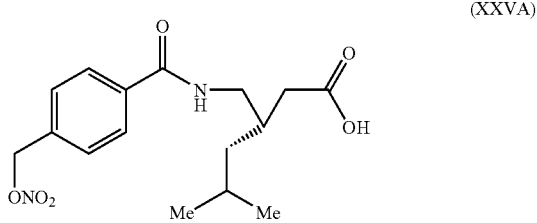

3-(S)-[3-(nitrooxymethyl)benzoylaminomethyl]-5-methyl-hexanoic acid (XXVIA),

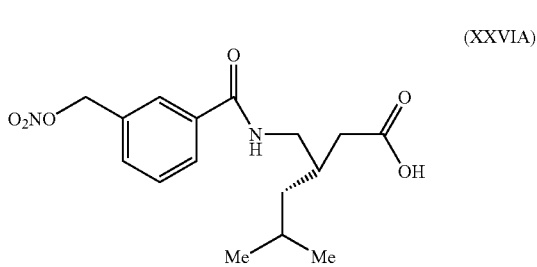

3(S)-[2-(nitrooxymethyl)benzoylaminomethyl]-5-methyl-hexanoic acid (XXVIIA),

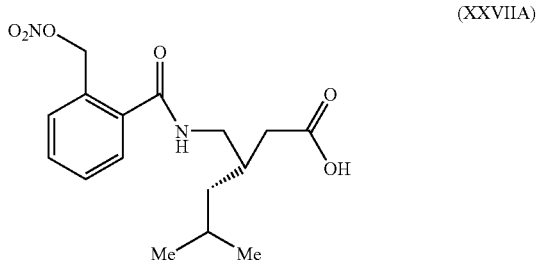

3(S)-[4-(nitrooxybutanoyl)aminomethyl]-5-methyl-hexanoic acid (XXVIIIA),

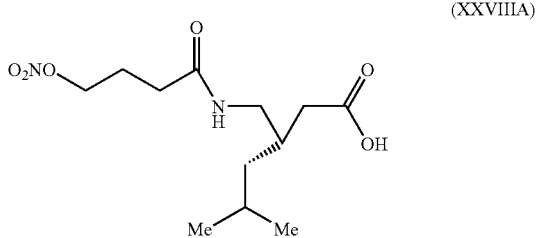

3(S)-[4-(nitrooxymethoxycarbonyl)aminomethyl]-5-methyl-hexanoic acid (XXIXA),

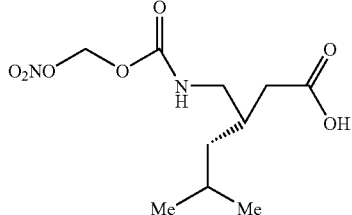

3(S)-{[2-(nitrooxymethyl)benzoyloxy]methoxycarbonylaminomethyl}-5-methyl-hexanoic acid (XXXA),

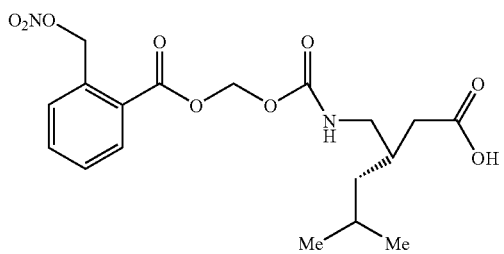

3(S)-{[3-(nitrooxymethyl)benzoyloxy]methoxycarbonylaminomethyl}-5-methyl-hexanoic acid (XXXIA),

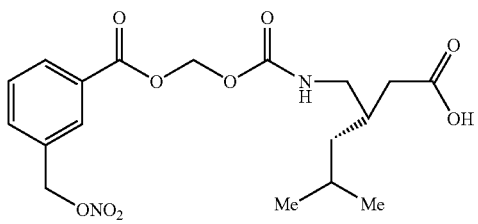

3(S)-{[4-(nitrooxymethyl)benzoyloxy]methoxycarbonylaminomethyl}-5-methyl-hexanoic acid (XXXIIA),

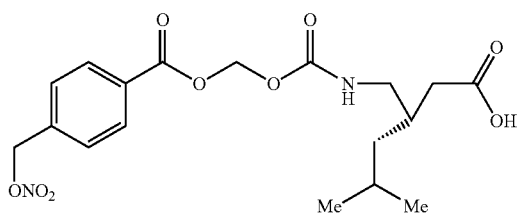

3(S)-[(3-nitrooxymethyl)phenoxycarbonylaminomethyl]-5-methyl-hexanoic acid (XXXIIIA),

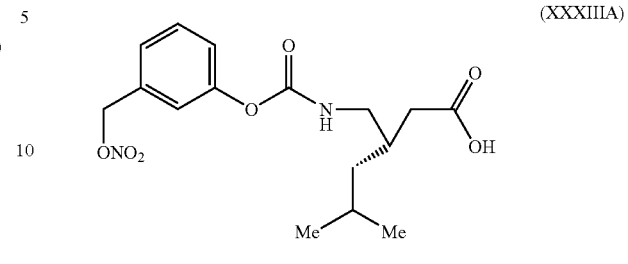

3(S)-{2-methoxy-4-[(1E)-3-[4-(nitrooxybutoxy]-3-oxa-1-propenylphenoxy]carbonyl-aminomethyl}-5-methyl-hexanoic acid (XXXIVA),

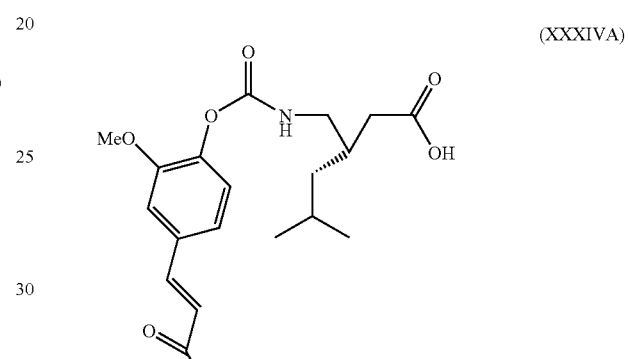

1-[4-(nitrooxybutyloxycarbonyl)aminomethyl]-cyclohexaneacetic acid (XXXVA),

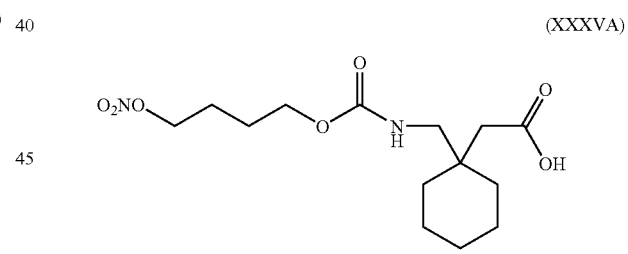

The compounds of the invention can be used also in form of the corresponding salts with pharmacologically acceptable cations, such as the salts of alkali metals.

Having a salifiable nitrogen atom within their molecule, for example when in formula (I) c0=1 and Y=moiety of formula (III), the compounds of the present invention can be transformed into the corresponding salts by reaction in an organic solvent, such as acetonitrile, tetrahydrofuran, with an equimolar amount of a corresponding organic or inorganic acid. Examples of organic acid are oxalic, tartaric, maleic, succinic and citric acids. Examples of inorganic acids are nitric, hydrochloric sulphuric and phosphoric acids. Preferred are the nitrate salts.

The compounds of the invention have shown to possess an improved activity for treatment of the chronic pain, in particular neurophatic pain, both as central and peripheric nervous system is concerned. Moreover, it has been surprisingly found that the compounds of the invention have an improved effect not only reducing neurophatic pain, but also showing unexpectedly a check on pathologic condition progress inducing neurophatic pain. When for example the drugs of the present invention are administered to diabetic subjects for diabetic neurophatic pain therapy, it has been found that said compound are able not only to reduce neuropathies, but also to lower diabetes induced complications, for example on blood vessels and/or renal apparatus.

The compounds of the present invention are in particular effective in treating neurophatic pain, for example diabetic nauropathic pain and post-infarct pain.

The compounds of the invention can be also employed in combination or in admixture with well known NO-donors. Said compounds contain for example one or more $ONO_2$ or ONO groups within their molecule.

NO-donors that may be used in association with the invention compounds should meet the in vitro test described here below. This text relates the generation of nitric oxide by NO-donors when in presence of endothelial cells (method a) or platelets (method b), for example nitro-glycerine, nicorandil, nitroprussiate, etc.

a) Endothelial Cells

Plated human umbilical vein cells with density of $10^3$ cells/well, have been incubated 5 minutes with NO-donor scalar concentrations (1-100 µg/ml). Incubation medium (physiological solvent, i.e. Tyrode) has been then analysed to ascertain the ability to generate NO by means of:

1) nitric oxide detection by chemiluminescence, 2) cGMP determination (cyclic GMP No. 2715 of Merck Index mentioned above).

As far as chemiluminescence analysis is concerned, a 100 µl aliquot has been injected into reaction chamber of an chemiluminescence analyzer containing glacial acetic acid and potassium iodide. The nitrites/nitrates present in medium in said conditions are converted in NO which is then revealed owing to its reaction with ozone, with consequent light production. As usual in devices measuring chemiluminescence, the produced luminescence is directly proportional to the generated NO levels and can be measured by means of the suitable photomultiplier unity of an chemiluminescence analyzer. The photomultiplier turns incident light into electric voltage, that then is quantitatively registered. Referring to a calibration curve, obtained with scalar nitrite concentrations, it has been possible to quantitatively evaluate the concentration of the generated NO. For example, from incubation of 100 µl nicorandil, an amount of about 10 µM NO was generated.

In order to determine cGMP, an amount of incubation medium (100 µl) was centrifuged 20 s at 1000 rpm. Surnatant was discarded and the sediment was treated with frozen phosphate buffer (pH 7.4). The cGMP produced levels were evaluated by immunoenzyme assay with specific reagents. From these experiments it results that in said experimental conditions the incubation with one of the several tested NO-donors caused a notable cGMP increase in comparison with the values obtained in absence of a NO-donor. For example, after incubation with 100 µM sodium nitroprussiate a 20 fold increase was registered in comparison with the corresponding value obtained incubating the vehicle alone without NO-donor.

b) Platelets

Washed human platelets have been used, obtained as described by Radomski et al., (Br. J. Pharmacol. 92, 639-1987). Amounts of 0.4 ml were incubated 5 minutes with scalar NO-donor concentrations (1-100 µg/ml). The incubation medium (i.e. Tyrode) was then analysed in order to determine the ability to generate NO by revealing nitric oxide with chemiluminescence technique and cGMP determination using the procedure previously described for the analysis carried out on endothelial cells. As to the chemiluminescence assay, also in this case on the basis of a calibration curve plotted with nitrite scalar concentrations, it has been possible to quantitatively define the concentration of the generated NO. For example, after incubation of 100 µM nicorandil, an amount of 35 µM of NO was generated.

For determining cGMP, also in these experimental conditions it resulted that the incubation with one of the several tested NO-donors caused a notable cGMP increase in comparison with the values obtained in absence of a NO-donor. For example, after incubation with 100 µM sodium nitroprussiate a 30 fold increase was registered in comparison with the value obtained incubating the vehicle alone without NO-donor.

The preferred NO-donors are those containing within the molecule radicals of the following drugs: aspirin, salicylic acid, ibuprofen, paracetamol, naproxen, diclofenac, flurbiprofen. These preferred compounds are synthesized as described in patent applications WO 95/20641, WO 97/16405, WO 95/09831, WO 01/12584.

The compounds of the invention can be obtained according to the synthesis procedures described here below.

Generally, should in the drug molecule several reactive groups be present, such as COOH and/or HX, wherein X is O, S or NH, they can be protected before the reaction according to the procedures known from literature, for example as described by Th. W. Greene in "Protective Groups In Organic Synthesis", Harvard University Press, 1980. However, protection of these groups is not strictly necessary for obtaining the compounds of the present invention.

For preparing the compounds of the present invention, when k0=0 the analgesic drug amine function was reacted with a reactive compound of linker C precursor, if b0=0, or of linker B precursor when b0=1.

When in formula (I) b0=0, the analgesic drug was generally reacted with one of the following compounds:

1. if k0=0 and the binding function with the analgesic drug is an amide function, the compound reacting with the drug was obtained as follows.

Starting compounds are acyl halides of formula Hal-$Y_1$—CO-Hal, wherein $Y_1$ is Y as defined above but without the oxygen atom binding $NO_2$ and Hal=Cl, Br, I. These compounds, when not available on the market, may be obtained according to a process well known in the art, for example from corresponding acids with thionyl or oxalyl chloride, $P^{III}$ or $P^{IV}$ halides, in solvents inert at the reaction conditions such as toluene, chloroform, DMF etc.

The acyl halide having the formula reported above, was reacted with a carboxylic group condensing agent, such as N-hydroxysuccinimide (SIMD-N—OH) according to methods known from the art, for example in halogenated solvents in the presence of a base at room temperature, obtaining N-hydroxysuccinimide ester as illustrated in the following reaction scheme:

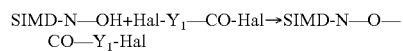

1a. The hydroxysuccinimide ester was reacted with the amine function of the analgesic drug at room temperature in alco holic and/or chlorinated solvents, in presence of an organic or inorganic base according to the following scheme:

$$\text{SIMD-N-O-CO-}Y_1\text{-Hal} + RNR_{1c}H \rightarrow R\text{-NR}_{1c}\text{-CO-}Y_1\text{-Hal} \quad (2A)$$

1-1. Alternatively, instead of employing the above mentioned acyl halides, hydroxy acids can be used having the formula HO—$Y_1$—COOH, wherein $Y_1$ is as defined above, that were reacted with N-hydroxysuccinimide in presence of an agent activating the carboxylic group, such as DCC, in halogenated solvents at room temperature according to the following scheme:

$$\text{SIMD-N-OH} + \text{HO-}Y_1\text{-COOH} \rightarrow \text{SIMD-N-O-CO-}Y_1\text{-OH}$$

1-1.a The compound obtained in 1-1 was reacted with the amine function of the analgesic drug at the conditions mentioned in 1a according to the following scheme:

$$\text{SIMD-N-O-CO-}Y_1\text{-OH} + RNR_{1c}H \rightarrow R\text{-NR}_{1c}\text{-CO-}Y_1\text{-OH} \quad (2B)$$

1b. When in formula (I), k0=1 with K=CO, the bond function with the analgesic drug is a carbamic function. Drug $RNR_{1c}H$ was reacted with an halogenformiate of formula Hal-$Y_1$—OCO-Hal, wherein $Y_1$ is as defined above.

Generally, the employed halogenformiate is available on the market or it can be obtained from the corresponding alcohols by reaction with triphosgene in presence of an organic base according to methods well known form the art. The reaction of halogenformiate with drug is carried out in a solvent mixture at room temperature and in presence of a base, for example in water and dioxane or methylene chloride and DMF. The reaction scheme is the following:

$$\text{Hal-}Y_1\text{-OCO-Hal} + RNR_{1c}H \rightarrow R\text{-NR}_{1c}\text{-CO-O-}Y_1\text{-Hal} \quad (2C)$$

1c. Preparation of nitrooxyderivatives from amides and carbamates obtained with the procedures mentioned above (b0=0)

When compounds obtained with the reaction described above have the formula R—$NR_{1c}$—CO—$Y_1$-Hal(2A) or R—$NR_{1c}$—CO—O—$Y_1$-Hal(2C), the corresponding nitrooxyderivatives have been prepared reacting (2A) or (2C) with $AgNO_3$ in an organic solvent such as acetonitrile, tetrahydrofuran, at a temperature of from 20° to 100° C. according to the scheme:

$$R\text{-NR}_{1c}\text{-CO-}Y_1\text{-Hal}(2A) + AgNO_3 \rightarrow R\text{-NR}_{1c}\text{-CO-}Y_1\text{-NO}_2$$

$$R\text{-NR}_{1c}\text{-CO-O-}Y_1\text{-Hal}(2C) + AgNO_3 \rightarrow R\text{-NR}_{1c}\text{-CO-O-}Y_1\text{-NO}_2$$

When compounds obtained with the reactions described above have the formula R—$NR_{1c}$—CO—$Y_1$—OH (2B), the hydroxyl group was subjected to halogenation, for example with $PBr_3$, $PCl_5$, $SOCl_2$, $PPh_3+I_2$ at room temperature, then it was reacted with $AgNO_3$ in an organic solvent, such as acetonitrile, tetrahydrofuran at the conditions mentioned above. Nitrooxyderivatives having the formula R—$NR_{1c}$—CO—$Y_1$—$NO_2$ were obtained.

1d. When in formula (I), b0=0, k0=1 and for example K=(1C), the following steps were performed. The amine function of the drug was reacted with the commercially available chloromethyl chloroformiate $ClC(O)OCH_2Cl$. The compound R—$NR_{1c}$—(CO)—$OCH_2Cl$ thus obtained was redacted with HO—$Y_1$—COOH in basic medium as indicated in 1a to give a compound of formula R—$NR_{1c}$—K—(CO)—$Y_1$—OH, that was then reacted as above in 1c to give the corresponding nitrooxyderivative.

2. When in formula (I), b0=c0=1, the synthesis to give the corresponding nitrooxyderivatives involves three steps. In first step, amides (in formula (I) k0=0) having substituents containing Hal groups (Hal=Cl, Br, I) or carbamates (in formula (I) k0=1) having substituents containing Hal groups as specified below were obtained.

2a. For preparing halogen-substituted amides, the amine function of the drug was reacted with a N-hydroxysuccinimide ester obtained from an acyl halide of formula P—$X_2$—COHal, wherein:

$X_2$ and Hal are as defined above,

P=HX in which X is as defined above or a carboxylic group protected for example with the corresponding tert-butyl ester, with N-hydroxysuccinimide (SIMD-N—OH) according to methods known in the art, for example at room temperature in halogenated solvents, in presence of a base, to give the compound of formula R—$NR_{1c}$—CO—$X_2$—P that, when P=HX, was reacted with a compound of formula Hal-$Y_1$—CO-Hal wherein Hal and $Y_1$ are as defined above. The reaction scheme is reported here below:

$$\text{SIMD-N-OH} + P\text{-}X_2\text{-COHal} \rightarrow \text{SIMD-N-O-CO-}X_2\text{-P}$$

$$\text{SIMD-N-O-CO-}X_2\text{-P} + RNR_{1c}H \rightarrow R\text{-NR}_{1c}\text{-CO-}X_2\text{-P} \quad (3A)$$

$$R\text{-NR}_{1c}\text{-CO-}X_2\text{-XH} + \text{Hal-}Y_1\text{-COHal} \rightarrow R\text{-NR}_{1c}\text{-CO-}X_2\text{-X-CO-}Y_1\text{-Hal} \quad (3A')$$

When in formula (3A) P=ester group as defined above, the carboxylic function can be restored with known procedures, for example reacting with anhydrous HCl in ethyl acetate or dioxane if the starting ester is tert-butyl ester. The acid thus obtained was reacted with a halogenated alcohol of formula Hal-$Y_1$—OH. The halogenated alcohol are available on the market.

2a.1 Alternatively, the drug $RNR_{1c}H$ was reacted with a N-hydroxysuccinimide ester, obtained from an acid of formula P—$X_2$—COOH, wherein P and $X_2$ are defined above, and N-hydroxysuccinimide (SIMD-N—OH), in presence of dicyclohexylcarbodiimide or another condensing agent according to methods well known in the art, for example at room temperature in halogenated solvents to give compound R—$NR_{1c}$—CO—$X_2$—P (3A) as for the following scheme:

$$\text{SIMD-N-OH} + P\text{-}X_2\text{-COOH} \rightarrow \text{SIMD-N-O-CO-}X_2\text{-P}$$

$$\text{SIMD-N-O-CO-}X_2\text{-P} + RNR_{1c}H \rightarrow R\text{-NR}_{1c}\text{-CO-}X_2\text{-P} \quad (3A)$$

Compound of formula (3A) was then reacted as described in 2a to give (3A').

2b. Preparation of halogen-substituted carbamates

From compound Hal-$Y_1$—O—CO—$X_2$—XH (4A) and triphosgene in presence of an organic base a halogenformiate of formula Hal-$Y_1$—O—CO—$X_2$—XCO-Hal was prepared according to the scheme reported in 1b. Compound (4A) was obtained reacting an alcohol of formula Hal-$Y_1$—OH with HX—$X_2$—COOH. The halogenformiate thus obtained was reacted with the drug amine function according to well known procedures, for example in DMF and/or methylene chloride in presence of a base at room temperature as for the following scheme:

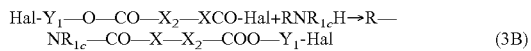 (3B)

2c. Preparation of nitrooxyderivatives from amides and carbamates obtained in 2a or 2b. Compounds (3A') or (3B) react in an organic solvent, such as acetonitrile, tetrahydrofuran, through end standing halogen with $AgNO_3$ to give the corresponding nitrooxyderivatives.

Applicant has surprisingly and unexpectedly found that compounds of the present invention show a higher activity on chronic pain than the corresponding precursors.

When compounds of the present invention contain one or more chiral centres, they can be employed in racemic form, as diastereomer or enantiomer mixture, as pure enantiomers or diastereomers. Should the compounds have geometric asymmetry, said compounds can be used in cis or trans form.

The compounds of the present invention are formulated in the corresponding pharmaceutical compositions for oral, parenteral and topic administration according to techniques well known in the art with usual excipients: for example as described in "Remington's Pharmaceutical Sciences $15^{th}$ Ed.".

The amount on molar basis of the active ingredient in these compositions is equal or lower then the maximal amount expected for precursor drugs. Due to the excellent tolerability, higher doses can also be employed. The daily doses to be administered are those of the precursor drugs or eventually lower. Said daily doses can be found for example in "Physician's Desk Reference".

The following examples are to further illustrate but not limit the scope of the present invention.

EXAMPLES

Example 1

Synthesis of 1-[4-(nitrooxymethyl)benzoylaminomethyl]cyclohexaneacetic acid (formula XVA)

A) Synthesis of N-hydroxysuccinimidyl 4-(chloromethyl)benzoate

To a solution of N-hydroxysuccinimide (1.375 g, 11.94 mmol) in methylene chloride (30 ml) triethylamine was added (1.66 ml, 11.94 mmol). To the solution thus obtained, cooled in a water/ice bath, slowly a solution of 4-(chloromethyl)benzoyl chloride (2.26 g, 11.94 mmol) in methylene chloride (20 ml) was added. When the adding was over, the mixture was allowed to stand overnight at room temperature. The mixture was then dried under vacuum to give 4.84 g of a white solid (mixture of the desired compound and triethylammonium chloride with quantitative yield) that was employed in the next reaction without further purification.

B) Synthesis of 1-[4-(chloromethyl)benzoylaminomethyl]cyclohexaneacetic acid

To a suspension of 1-(aminomethyl)cyclohexaneacetic acid (gabapentin, 2.25 g, 13.13 mmol) in absolute ethanol (100 ml) triethylamine was added (3.66 ml, 26.27 mmol) to give a clear solution. In the solution thus obtained and cooled in a water/ice bath, a solution of the equimolar mixture of triethylammonium chloride and N-hydroxysuccinimidyl 4-(chloromethyl)benzoate (4.84 g, 11.94 mmol) in methylene chloride (100 ml) obtained in A) was dropped. After stirring about 4 hours at room temperature, to the mixture ethyl acetate was added (100 ml) and the solution was extracted with a 4% water solution of hydrochloric acid. The organic phase was dried under vacuum to give 3.85 g of the desired product as a white solid.

C) Synthesis of 1-[4-(nitrooxymethyl)benzoylaminomethyl]cyclohexaneacetic acid

To a suspension of 1-[4-(chloromethyl)benzoylaminomethyl]cyclohexaneacetic acid (4.01 g, 12.39 mmol) in acetonitrile (250 ml) silver nitrate was added (2.11 g, 12.39 mmol). The mixture was stirred at 60° C. under vacuum out of light adding silver nitrate in five aliquots within about 20 hours. The mixture was heated for 24 hours, adding other 5 equivalents of the silver nitrate further to those already added. The salt thus formed was filtered off, to the mixture ethyl acetate (200 ml) and a 2% hydrochloric acid solution were added. The precipitated insoluble salts were filtered off and the organic phase was dried under vacuum. The raw material thus obtained was purified by silica gel chromatography with n-hexane/ethyl acetate 6/4 (v/v) as eluent. The product thus obtained was crystallized from ethyl acetate/n-hexane to give 2.45 g of a white solid with m.p=127-128° C.

$^1$H-NMR (CDCl$_3$) ppm: 7.86 (2H, d); 7.50 (2H, d); 7.06 (1H, t); 5.49 (2H, s); 3.54 (2H, d); 2.43 (2H, s); 1.53 (10H, m).

Example 2

Synthesis of 1-(nitrooxymethoxycarbonylaminomethyl)cyclohexaneacetic acid (formula XIXA)

A) Synthesis of 1-(chloromethoxycarbonylaminomethyl)cyclohexaneacetic acid

To a solution of 1-(aminomethyl)cyclohexaneacetic acid (gabapentin, 2.00 g, 11.68 mmol) in a water (30 ml) and dioxane (20 ml) mixture, diisopropylethylamine was added (4.06 ml, 23.36 mmol). In the solution thus obtained, and cooled in a water/ice bath, chloromethyl chloroformiate (1.25 ml, 14.02 mmol) dissolved in dioxane (20 ml) was slowly dropped. At the end of adding, the mixture was allowed to stand 3 hours at room temperature. The mixture was then poured in a 4% hydrochloric acid solution to sink the end pH value to about 2. Ethyl acetate was added and the organic phase<was dried under vacuum to give 2.87 g of a clear, yellow oil that was employed in the next reaction without further purification.

B) Synthesis of 1-(nitrooxymethoxycarbonylaminomethyl)cyclohexaneacetic acid

To a solution of 1-(chloromethoxycarbonylaminomethyl) cyclohexaneacetic acid (2.87 g, 10.92 mmol) in acetonitrile (25 ml) silver nitrate was added (3.71 g, 21.84 mmol). The mixture was stirred 3 hours under vacuum out of light at 40° C. The precipitated salt was filtered off and to the mixture ethyl acetate (30 ml) and a 2% hydrochloric acid solution were added. The salts thus formed was removed by filtration and the organic phase was dried under vacuum. The oily product thus obtained was purified by silica gel chromatography with n-hexane/ethyl acetate 6/4 (v/v) as eluent to give 2.68 g of colourless oil, $^1$H-NMR (CDCl$_3$) ppm: 6.03 (2H, s); 5.51 (1H, t); 3.30 (2H d), 2.36 (2H, s); 1.47 (10H, m).

Example 3

Synthesis of 1-[3-(nitrooxymethyl)phenoxycarbonylaminomethyl)cyclohexaneacetic acid (formula XXIIIA)

A) Synthesis of 1-[3-(bromomethyl)phenoxycarbonylaminomethyl)cyclohexaneacetic acid To a suspension of 3-bromomethylphenol (0.50 g, 2.67 mmol) in methylene chloride (8 ml), bis(trichloromethyl) carbonate (triphosgene, 0.368 g, 1.24 mmol) dissolved in methyl chloride (2 ml) and diisopropylethylamine (0.466 ml, 2.67 mmol) were cool added. The solution thus obtained was stirred one night at room temperature and then refluxed for 2 hours, This cooled solution was then dropped in a suspension of 1-(aminomethyl)cyclohexaneacetic acid (gabapentin, 0.911 g, 5.35 mmol) and diisopropylethylamine (0.932 ml, 5.35 mmol) in anhydrous dimethylformamide (4 ml). After 3 hours stirring, to the mixture ethyl acetate was added and it was washed with a 4% hydrochloric acid solution. The organic phase was dried under vacuum and the raw product thus obtained was purified by silica gel chromatography with n-hexane/ethyl acetate 1/1 (v/v) as eluent. The desired product was obtained as an oil (0.100 g) that was employed without further purification.

B) Synthesis of 1-[3-(nitrooxymethyl)phenoxycarbonylaminomethyl)cyclohexane-acetic acid To a suspension of 1-[3-(bromomethyl)phenoxycarbonylaminomethyl)cyclo-hexaneacetic acid (0.100 g, 0.26 mmol) in acetonitrile (2 ml) silver nitrate was added (0.100 g, 0.59 mmol). The mixture was stirred overnight at room temperature under nitrogen atmosphere out of light. The salt thus formed was filtered off and to the mixture ethyl acetate (5 ml) and a 2% hydrochloric acid solution were added. Insoluble salts were filtered off and the organic phase was purified by silica gel chromatography with methylene chloride/methanol 97/3 (v/v) as eluent, to give 0.080 g of product as an oil.

$^1$H-NMR (CDCl$_3$) ppm: 7.38 (1H, t); 7.22 (3H, m); 5.68 (1H, t); 5.43 (2H, s); 3.34 (2H, d); 2.41 (2H, s); 1.49 (10H, m).

Example 4

Synthesis of 1-[4-(nitrooxybutyloxycarbonyl)aminomethyl]cyclohexaneacetic acid (formula XXXVA)

A) Synthesis of 1-[4-(chlorobutyloxycarbonyl)aminomethyl]cyclohexaneacetic acid To a solution of 1-(aminomethyl)cyclohexaneacetic acid (1.95 g, 11.4 mmol) in dioxane/water (1:1, 40 ml), N,N-diisopropylethylamine was added (4.00 ml, 23.0 mmol) and the solution was cooled at 0° C. Then 1-chlorobutyl chloroformiate was slowly added (1.30 ml, 9.50 mmol) and the reaction was allowed to reach room temperature and maintained 5 hours under stirring. The mixture was diluted with methylene chloride and washed with 4% aqueous hydrochloric acid, dehydrated and dried under vacuum, to give 2.87 g of an colourless oil that was employed in the next reaction without further purification.

B) Synthesis of 1-[4-(iodobutyloxycarbonyl)aminomethyl]cyclohexaneacetic acid To a solution of 1-[4-(chlorobutyloxycarbonyl)aminomethyl]cyclohexaneacetic acid (1.68 g, 5.70 mmol) in acetonitrile (20 ml), sodium iodide was added (8.48 g, 57.0 mmol) and the reaction mixture was refluxed 5 hours under stirring. The solvent was then removed under vacuum and the residue treated with methylene chloride. The organic phase was washed with water, dehydrated and dried under vacuum to give 2.12 g of an oily product that was employed in the next step without purification.

C) Synthesis of 1-[4-(nitrooxybutyloxycarbonyl) aminomethyl]cyclohexaneacetic acid To a solution of 1-[4-(iodobutyloxycarbonyl)aminomethyl]cyclohexaneacetic acid (2.12 g, 5.30 mmol) in acetonitrile (25 ml), silver nitrate was added (2.42 g, 14.2 mmol). The mixture was stirred 5 hours at 40° C. under nitrogen atmosphere and out of light, then it was filtered on celite and concentrated. The residue was treated with methylene chloride and extracted with a 4% hydrochloric acid solution. The salts thus formed were filtered off and the aqueous phase was extracted with methylene chloride. The organic phases were washed with a saturated sodium chloride solution, dehydrated and dried under vacuum. The oily residue was dissolved in ethyl ether, filtered on celite and dried under vacuum to give 1.64 g of an oily product.

$^1$H-NMR (CDCl$_3$) ppm: 5.65 (1H, m); 4.49 (2H, t); 4.12 (2H, t); 3.23 82H, d); 2.34 (2H, s); 1.9-1.7 (4H, m); 1.6-1.3 (10H, m).

Example F1

Evaluation of Analgesic Activity of the Compounds of the Invention by Writhing Test (Vinegar et al., 1979)

Nine groups of male Swiss mice (20-25 g, Charles River), 10 animals each, received by oral administration through gastric tube (gavage) gabapentin in an amount of from 1 to 10 mg/kg or the compound of the invention (XVA, Example 1), hereinafter NO-gabapentin, in an amount of from 1 to 10 mg/kg dissolved in saline solution. One hour after administration of the compound solutions, through intraperitoneal injection the mice received a glacial acetic acid solution (0.5 ml, 0.6%). Within 15 minutes subsequent to the administration of acetic acid, in every animal the number of abdominal contractions was counted. Analysis was carried out in blind.

The results reported in Table 1 are given as the number of total contractions within the observation time (15 minutes). The results show that NO-gabapentin is more active than precursor drug in inhibiting abdominal contraction amount.

Example F2

Evaluation of Analgesic Activity of the Compounds of the Invention by Paw Licking Test Three groups of male Swiss mice (20-25 g, Charles River), 10 animals each, received by oral administration as in Example F1 gabapentin in an amount of 3 mg/kg (17.5 μm/kg) or the compound of formula (XVA, Example 1), hereinafter NO-gabapentin, in an amount of 3 mg/kg (8.5 μm/kg) dissolved in saline solution. The control group received an equal volume of saline solution. One hour after administration of the compound solutions, the mice were injected with formalin in the paw (10 μl).

The formalin injection induced a biphasic reaction. In first phase (phase I, 0-15 minutes) an acute inflammation was observed; in the second phase (phase II, 15-30 minutes) a release of chemical mediators occurred as in neurophatic pain. Within 30 minutes subsequent to formalin injection, in each animal the time in seconds in which the animal licked its paw was recorded. Analysis was carried out in blind.

The results reported in Table 2 are expressed as the entire time in seconds in which paw licking in animals during the first and second phase as defined above was observed.

The results show that NO-gabapentin is more active than the starting drug in inhibiting paw licking in first phase even though administered at a molar dose corresponding to 50% of gabapentin. For this reason, in second phase NO-gabapentin is less effective.

Example F3

Evaluation of Analgesic Activity of the Compounds of the Invention in Animal Models of Neuropathic Pain We have tested the antinoceptive effects of compound of formula (XVA, Example 1), hereinafter NO-gabapentin, in the model of neuropathic pain constituted by the chronic constriction injury of the rat sciatic nerve. The parent compound gabapentin has been used as reference drug.

The unilateral periphal mononeuropathy was obtained according to the method described by Bennet G J and Xie Y K, Pain (33) 1988: 87-107. Sample populations ranging from 8 to 12 rats (SD males weighting 250-300 g) for condition were used. The antinoceptive effect of the drugs was determined by measuring the vocalization threshold (VTPP) elicited by paw pressure both at the injured and at the controlateral side. The test was performed at day 14 post lesion. All compounds were tested for acute antinoceptive effects. Acute effects were determined within 60 min following a single intraperitoneal (i.p.) injection of the drugs prior to the test.

Each group of the rats received gabapentin at the dose of 30 mg/kg (175 μmoles/kg), or an equimolar dose of NO-gabapentin (175 μmoles/kg), or the same volume of vehicle (Control group). The drugs were dissolved (20 mg/mL) in vehicle containing saline: DMSO: Castor oil (68:8:24).

The results are reported in Table 3 and show that NO-gabapentin was more efficacious than gabapentin.

TABLE 1

Evaluation of gabapentin and NO-gabapentin analgesic activity in experiment F1 (writhing test)

| Treatment | Dose (mg/kg) | Contractions number |
| --- | --- | --- |
| Controls | — | 39 |
| Gabapentin | 1 | 32 |
| NO-gabapentin | 1 | 24 |
| Gabapentin | 3 | 22 |
| NO-gabapentin | 3 | 15 |
| Gabapentin | 10 | 27 |
| NO-gabapentin | 10 | 15 |

TABLE 2

Evaluation of gabapentin and NO-gabapentin analgesic activity in experiment F2 (formalin injected in rats paw)

| Treatment | Dose (μm/kg) | paw licking (sec) Phase I | Phase II |
| --- | --- | --- | --- |
| Controls | — | 125 | 185 |
| Gabapentin | 17.5 | 85 | 30 |
| NO-gabapentin | 8.5 | 50 | 60 |

TABLE 3

Evaluation of gabapentin and NO-gabapentin analgesic activity in experiment F3 (model of neuropathic pain)

| Time Post-dosing (min) | Vocalization threshold to pressure in the injured paw (VTPP) (grams) | | |
| --- | --- | --- | --- |
| | Control | gabapentin (175 μmoles/kg, ip) | NO-gabapentin (175 μmoles/kg, ip) |
| 0 | 144 ± 10 | 160 ± 10 | 153 ± 10 |
| 5 | 156 ± 10 | 165 ± 23 | 187 ± 10 |
| 10 | 162 ± 14 | 191 ± 29 | 307 ± 14 |
| 20 | 150 ± 08 | 250 ± 24 | 325 ± 08 |
| 40 | 159 ± 11 | 266 ± 26 | 390 ± 11 |
| 60 | 150 ± 09 | 250 ± 38 | 382 ± 09 |

The invention claimed is:

1. Nitrooxyderivatives or salts thereof of formula (I)

$$R-NR_{1c}(K)_{k0}-(B)_{b0}-(C)_{c0}-NO_2 \qquad (I)$$

wherein c0 is 1;

b0 is 0;

k0 is 1;

$R_{1c}$ is H;

K is the bivalent radical (1C) of the formula:

(1-C)

$R_t$ and $R'_t$, same or different, are H, $C_1$-$C_{10}$-alkyl, phenyl or benzyl, —COOR$_y$, in which $R_y$=H, $C_1$-$C_{10}$-alkyl, phenyl, or benzyl;

C=bivalent radical of formula -$T_c$-Y wherein $T_c$=(CO);

Y is an alkylenoxy group —R'O— in which R' is straight or branched $C_1$-$C_{20}$ or a cycloalkylene with from 5 to 7 carbon atoms;

—(CH$_2$)$_{n3'}$—O—
—(CH$_2$)$_{n3}$ wherein n3 is an integer from 0 to 5 and n3' is an integer from 1 to 3;

R is the radical of an analgesic drug of formula (II):

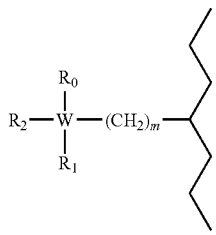
(II)

wherein:
W is a carbon atom;
m is 1;
$R_0$=—$(CH_2)_n$—$COOR_y$, wherein $R_y$=H, $C_1$-$C_{10}$-alkyl, phenyl, or benzyl;
n is an integer of from 0 to 2;
$R_1$=H;
$R_2$ is:
   a radical of formula (IIA), wherein optionally an ethylenic unsaturation may be present between the carbon atoms in position 1 and 2:

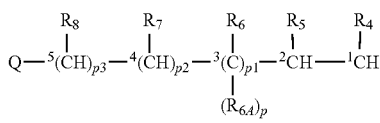
(IIA)

wherein:
p, $p_1$, $p_2$ are 0;
$p_3$ is 0;
$R_4$ is hydrogen;
$R_5$ is hydrogen or a straight or branched $C_1$-$C_6$-alkyl,
Q is straight or branched $C_1$-$C_6$-alkyl; or
in formula (II) $R_2$ and $R_1$ with W together form a $C_4$-$C_{10}$ saturated or unsaturated ring.

2. Compounds according to claim 1, wherein:
in formula (II):
n=1, $R_y$=H;
$R_1$ and $R_2$ with W form a cyclohexane ring; the drug precursor of R having the formula R—$NH_2$ is known as gabapentin; or
in formula (II):
n=1, $R_y$=H,
$R_1$=H
$R_2$ is the radical of formula (IIA) in which $R_5$=Q=$CH_3$; the drug precursor of R having the formula R—$NH_2$ is known as (S)-3-isobutilGABA.

3. Compounds according to claim 1 selected from:
1-{[4-(nitrooxymethyl)benzoyloxy]methoxycarbonylaminomethyl}-cyclohexaneacetic acid (XXA), (XXA)
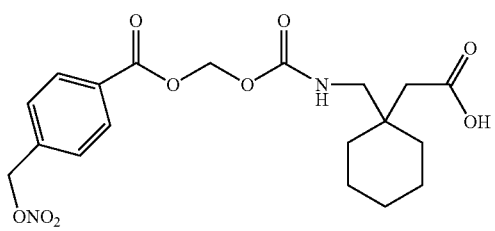

1-{[3-(nitrooxymethyl)benzoyloxy]methoxycarbonylaminomethyl}-cyclohexaneacetic acid (XXIA), (XXIA)
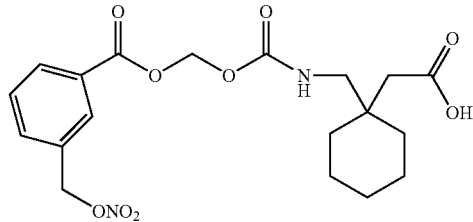

1-{[2-(nitrooxymethyl)benzoyloxy]methoxycarbonylaminomethyl}-cyclohexaneacetic acid (XXIIA), (XXIIA)
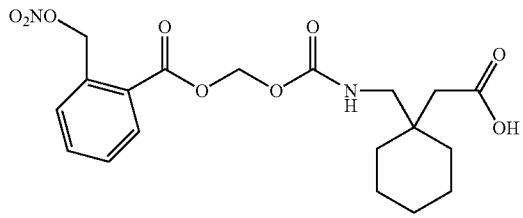

3(S)-{[2-(nitrooxymethyl)benzoyloxy]methoxycarbonylaminomethyl}-5-methyl-hexanoic acid (XXXA), (XXXA)
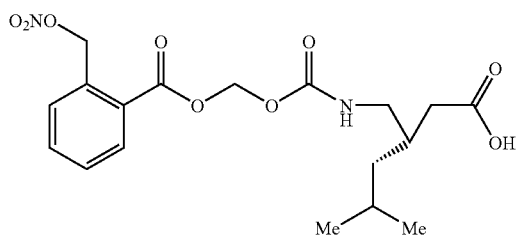

3(S)-{[3-(nitrooxymethyl)benzoyloxy]methoxycarbonylaminormethyl}-5-methyl-hexanoic acid (XXXIA), (XXXIA)
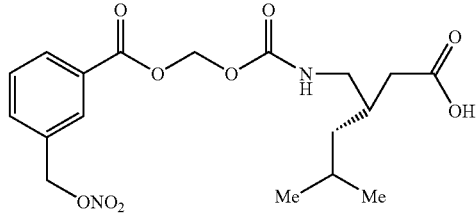

3(S)-[4-(nitrooxymethyl)benzoyloxy]methoxycarbonylaminomethyl}-5-methyl-hexanoic acid (XXXIIA), and (XXXIIA)
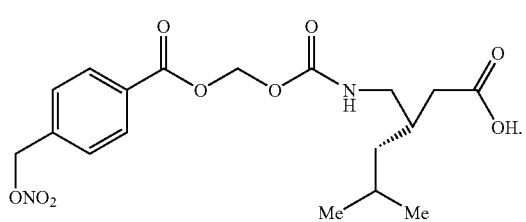

4. A composition comprising: a compound according to claim 1, and a NO-donor compound comprising a radical of a drug selected from the group consisting of: aspirin, salicylic acid, ibuprofen, paracetamol, naproxen, diclofenac and flurbiprofen and at least a group that is an —$ONO_2$ group or an —ONO group.

5. Pharmaceutical compositions comprising compounds according to claim 1 as active ingredients.

6. A method of treatment of chronic pain comprising administering an effective amount of the compounds according to claim 1.

7. The method according to claim 6, wherein the chronic pain is neurophatic pain.

\* \* \* \* \*